United States Patent
Schoeler et al.

(10) Patent No.: US 12,135,436 B2
(45) Date of Patent: Nov. 5, 2024

(54) METHOD FOR CENTERING AN OPTICAL ELEMENT IN AN OPTICAL SYSTEM FOR AN ENDOSCOPE

(71) Applicants: OLYMPUS WINTER & IBE GMBH, Hamburg (DE); FRAUN-HOFER-GESELLSCHAFT ZUR FOERDERUNG DERANGEWANDTEN FORSCHUNG E.V., Munich (DE)

(72) Inventors: Uwe Schoeler, Hoisdorf (DE); Erik Beckert, Arnstadt (DE)

(73) Assignees: OLYMPUS WINTER & IBE GMBH, Hamburg (DE); FRAUNHOFER-GESELLSCHAFT ZUR FOERDERUNG DERANGEWANDTEN FORSCHUNG E.V., Munich (DE)

( * ) Notice: Subject to any disclaimer, the term of this patent is extended or adjusted under 35 U.S.C. 154(b) by 1084 days.

(21) Appl. No.: 17/024,840

(22) Filed: Sep. 18, 2020

(65) Prior Publication Data

US 2021/0003805 A1    Jan. 7, 2021

Related U.S. Application Data

(63) Continuation of application No. PCT/EP2019/055535, filed on Mar. 6, 2019.

(30) Foreign Application Priority Data

Mar. 20, 2018   (DE) .......................... 102018106468.3

(51) Int. Cl.
*G02B 27/62* (2006.01)
*A61B 1/00* (2006.01)
(Continued)

(52) U.S. Cl.
CPC ............ *G02B 27/62* (2013.01); *A61B 1/0011* (2013.01); *A61B 1/00163* (2013.01);
(Continued)

(58) Field of Classification Search
CPC ....... G02B 27/62; G02B 7/003; A61B 1/0011; A61B 1/00163; G01B 11/272; G01B 11/27; G01M 11/0221
(Continued)

(56) References Cited

U.S. PATENT DOCUMENTS

| 9,638,836 B1* | 5/2017 | Harrison ............ G02B 27/0172 |
| 2015/0063764 A1* | 3/2015 | Isenhour ................ G02B 7/003 |
| | | 359/811 |
| 2017/0189991 A1 | 7/2017 | Gollier et al. |

FOREIGN PATENT DOCUMENTS

| CN | 1042679 A | 6/1990 |
| CN | 203804722 U | 9/2014 |

(Continued)

OTHER PUBLICATIONS

English abstract only of EP 0 366 356 A2.
International Search Report dated May 22, 2019 issued in PCT/EP2019/055535.

*Primary Examiner* — Dana Ross
*Assistant Examiner* — Joseph W Iskra
(74) *Attorney, Agent, or Firm* — Scully, Scott, Murphy & Presser, P.C.

(57) ABSTRACT

A method for preparing an optical element for insertion into an optical system of an endoscope, wherein the optical element has an optical axis and a peripheral surface that is basically parallel to the optical axis, the method including: arranging the optical element in a mounting of a spindle which rotates the optical element about an axis of rotation of the spindle, aligning the optical element on the spindle such that the optical axis of the optical element coincides with the (Continued)

axis of rotation of the spindle, and subsequent to the aligning, removing an outer peripheral surface region of the optical element until the peripheral surface has a constant spacing from the optical axis of the optical element, wherein the removing of the outer peripheral surface region takes place by laser ablation.

13 Claims, 4 Drawing Sheets

(51) Int. Cl.
*G01B 11/27* (2006.01)
*G01M 11/02* (2006.01)
*G02B 7/00* (2021.01)

(52) U.S. Cl.
CPC ....... *G01B 11/272* (2013.01); *G01M 11/0221* (2013.01); *G02B 7/003* (2013.01)

(58) Field of Classification Search
USPC .................................................. 219/121.72
See application file for complete search history.

(56) References Cited

FOREIGN PATENT DOCUMENTS

| | | |
|---|---|---|
| DE | 1034637 B | 7/1958 |
| DE | 10322587 A1 | 1/2005 |
| DE | 102005003595 A1 | 7/2006 |
| JP | H08-11043 A | 1/1996 |
| JP | 2002-103105 A | 4/2002 |
| JP | 2003-117702 A | 4/2003 |
| JP | 2007-033556 A | 2/2007 |
| JP | 2017-131384 A | 8/2017 |
| WO | WO 2010/111465 A1 | 9/2010 |
| WO | 2018/033775 A1 | 2/2018 |

* cited by examiner

METHOD FOR CENTERING AN OPTICAL ELEMENT IN AN OPTICAL SYSTEM FOR AN ENDOSCOPE

CROSS-REFERENCE TO RELATED APPLICATION

The present application is a continuation of PCT/EP2019/055535 filed on Mar. 6, 2019, which is based upon and claims the benefit to DE 10 2018 106 468.3 filed on Mar. 20, 2018, the entire contents of each of which are incorporated herein by reference.

BACKGROUND

Field

The present disclosure relates to a method for preparing an optical element for insertion into an optical system of an endoscope and a method for centering an optical element in an optical system of an endoscope. The present disclosure also relates to a centering and rotating device.

Prior Art

When using endoscopes, good image quality is necessary, for example, to enable doctors performing operations to have a good view of the field of operation. In video endoscopes, this requires the use of image sensors with increasingly high resolution. In order to utilize this higher resolution, the optical elements, for example the lenses, as well as their alignment in relation to each other in the endoscope also have to meet high standards. The optical axes of all the optical elements in the optical system of the endoscope thus have to coincide with the optical axis of the optical system as exactly as possible. If, however, the deviation of the optical axis of an optical element from the optical axis of the optical system is too great, the image quality of the endoscope decreases.

In order to bring the optical axes of the optical elements into congruence with the optical axis of the optical system, the optical elements are usually processed by means of a grinding process. Optical elements with a diameter tolerance of approximately 20 µm can thereby be provided. By inserting these optical elements into an optical frame of the optical system that has also been produced with high precision, the optical elements are aligned along the common optical axis.

By means of such a grinding method, however, the tolerances that are necessary when using high-resolution image sensors cannot be achieved. Instead, in this case the optical elements have until now been encased in a brass sleeve that is then turned with a special centering and rotating machine. In this manner, much smaller diameter tolerances are achieved.

By encasing in the brass sleeve, the diameter of the optical element is increased by approximately 200 µm to 300 µm, which in the design may make it necessary to increase the endoscope diameter or decrease the diameter of the optical element. In addition, the process can cause damage, for example chipping, in the turned surface of the sleeve. Finally, the centering and rotating process is time intensive and embedding the optical element in a brass sleeve causes additional costs.

FIG. 1 schematically shows an optical system 10 of an endoscope according to the prior art in cross-section. An optical element 20 is inserted in an optical frame 14 of the optical system 10. The optical element 20 is embedded in a sleeve 16, for example a brass sleeve. Since the mechanical axis of the brass sleeve 16 and the optical axis 22 of the optical element 20 do not coincide, the optical axis 12 of the optical system 10 and the optical axis 22 of the optical element 20 also do not coincide. To solve this problem, according to the prior art the brass sleeve 16 is processed through a centering and rotating process such that the optical axes 12 and 22 coincide. However, the centering and rotating method is very work intensive and requires the use of a sleeve 16, which limits the maximum diameter of the optical element 20.

SUMMARY

An object is to provide an improved method for preparing an optical element for insertion into an optical system of an endoscope, an improved method for centering an optical element in an optical system of an endoscope, an improved centering and rotating device, and an improved endoscope.

Such object can be achieved by a method for preparing an optical element for insertion into an optical system of an endoscope, wherein the optical element has an optical axis and a peripheral surface that is basically parallel to the optical axis, the method comprising:

arranging the optical element in a mounting of a spindle which rotates the optical element about an axis of rotation of the spindle, aligning the optical element on the spindle such that the optical axis of the optical element coincides with the axis of rotation of the spindle, removing an outer peripheral surface region of the optical element until the peripheral surface has a constant spacing from the optical axis of the optical element, wherein the removal of the outer peripheral surface region takes place by laser ablation, such as by means of an ultra-short pulse laser.

In contrast to a centering and rotating method according to the prior art, the typically used turning tool is replaced by a laser, such as an ultra-short pulse laser. The ultra-short pulse laser advantageously has a pulse duration in the femtosecond range. With such a laser, the removed material is removed more precisely than with a turning tool. Chipping during the turning process is also prevented. Since the ablation process occurs at the atomic level, a surface with a very low roughness can be generated Chamfering also takes place very precisely and reproducibly and without chipping.

The optical element can be made of an optically permeable material, wherein the optically permeable material is removed directly during the removal of the outer peripheral surface region. While the centering and rotating process with a turning tool can lead to chipping or require a sleeve to be used which takes up space, this is not necessary for removal by means of laser ablation.

The optical element can be made completely out of the optically permeable material, for example optical glass, and a sleeve can be omitted. This allows optical elements to be produced with a larger diameter than before, whereby more light is captured and the image quality of an endoscope with this optical element is improved. This also does not incur the costs of embedding the optical element into a sleeve. Alternatively, the diameter of the optical unit can be decreased overall while the amount of light remains the same, since space is no longer used up by brass sleeves.

The alignment of the optical element on the spindle can take place by means of at least one impact device, wherein the impact device changes the alignment of the optical axis of the optical element with respect to the axis of rotation of the spindle through impacts with an alignment unit connected to the mounting.

The alignment unit can be a component of the spindle. A first part of the alignment unit is arranged such that its alignment in relation to the axis of rotation of the spindle is fixed. A second part of the alignment unit which is mounted on the first part of the alignment unit can be directly connected to the mounting. The alignment of this second part of the alignment unit in relation to the axis of rotation of the spindle can be variable such that the alignment of the optical axis of one of the elements located in the mounting is changed in relation to the axis of rotation of the spindle by impacts of the impact device with the second part of the alignment unit. In this way, the optical axis of the optical element can be set extremely precisely in relation to the axis of rotation of the spindle.

The alignment of the optical element on the spindle can be checked by detecting a light signal on a photosensitive element of a signal detection device, wherein the light signal is generated in that a light beam is conducted along the axis of rotation of the spindle in the direction of the photosensitive element, wherein the alignment of the optical element is changed until a position of the light signal on the photosensitive element remains constant when the spindle is rotated.

If the alignment of the optical axis of the optical element deviates from the axis of rotation of the spindle, a light beam conducted along the axis of rotation of the spindle can describe a rotational movement on the photosensitive element. In this case, a circular movement of the detected light signal can be registered with the signal detection device. If the optical axis of the optical element lies exactly on the axis of rotation of the spindle, however, the position of the light beam on the photosensitive element remains constant. In this manner, it can be checked very exactly if the optical axis of the optical element coincides with the axis of rotation of the spindle.

Such object can be further achieved by a method for centering an optical element in an optical system of an endoscope, wherein the optical system has an optical axis and the optical element has an optical axis and a peripheral surface that is basically parallel to the optical axis, the method comprising:

removing an outer peripheral surface region of the optical element until the peripheral surface has a constant spacing from the optical axis of the optical element, inserting the optical element into the optical system, wherein the peripheral surface of the optical element abuts an inner surface of an optical frame of the optical system and the optical axis of the optical element coincides with the optical axis of the optical system, wherein the removal of the outer peripheral surface region of the optical element takes place by means of laser ablation, such as by the previously stated method for preparing an optical element for insertion into an optical system of an endoscope.

According to this method for centering an optical element in an optical system of an endoscope, the optical element can be inserted into the optical frame of the optical system without it being necessary to embed the optical element into a sleeve. The inner surface of the optical frame has a diameter that basically corresponds to the diameter of the optical element. Since the peripheral surface of the optical element has a constant spacing from the optical axis of the optical element after the removal of the outer peripheral surface region, the optical element is centered by the insertion of the optical element into the optical frame of the optical system such that the optical axis of the optical element coincides with the optical axis of the optical system.

Multiple optical elements can be inserted into the optical system, wherein the optical axes of all the optical elements are brought to coincide with the optical axis of the optical system and wherein the peripheral surfaces of all the optical elements abut the inner surface of the optical frame of the optical system. An extremely precise alignment of the optical axes of the optical elements and high image quality of the endoscope are achieved in that multiple optical elements, where all the optical elements of the optical system that have an optical axis, are processed in the described manner and inserted into the optical system.

The method for centering an optical element in an optical system of an endow scope also embodies the same advantages, features and characteristics as the previously described method for preparing an optical element for insertion into an optical system of an endoscope.

Such object can also be achieved by a centering and rotating device comprising a spindle that is rotatable about an axis of rotation with a mounting for an optical element for an endoscope and a removal device with a removal element which is configured to remove a peripheral surface of an optical element in the mounting, wherein, in a modification of the centering and rotating device, the removal element is a laser, such as an ultra-short pulse laser.

In a centering and rotating device according to the prior art, a turning tool is typically used as the removal element. This is advantageously replaced by a laser, such as an ultra-short pulse laser.

An impact device is also provided which is configured to change the alignment of the mounting with respect to the axis of rotation through impacts with an alignment unit connected to the mounting.

At least one signal detection device with a photosensitive element is also provided, wherein the photosensitive element is arranged such that a light signal of a light beam conducted along the axis of rotation of the spindle can be detected by the signal detection device.

The spindle can have a hydrostatic bearing. Advantageously, the rotation of the spindle takes place extremely precisely as a result of the hydrostatic bearing such that a change in the axis of rotation during the rotation is prevented.

The centering and rotating device also embodies the same advantages, features and characteristics as the previously described methods.

Such object can be further achieved by an endoscope with an optical element for insertion into an optical system of the endoscope, wherein the optical element has an optical axis and a peripheral surface that is basically parallel to the optical axis and wherein the optical element is prepared with a method for preparing an optical element according to one or more of the previously mentioned embodiments.

Such object can be further achieved by an endoscope with an optical element for insertion into an optical system of the endoscope, wherein the optical element has an optical axis and a peripheral surface that is basically parallel to the optical axis and wherein the optical element is centered with a method for centering an optical element according to one or more of the previously mentioned embodiments.

BRIEF DESCRIPTION OF THE DRAWINGS

Further features will become apparent from the description of the embodiments together with the claims and the attached drawings. Embodiments can fulfill individual features or a combination of several features.

The embodiments are described below, without restricting the general idea of the invention, using such embodiments with reference to the drawings, express reference being made to the drawings with regard to all details that are not explained in greater detail in the text. In the following.

In the drawings, the same or similar elements and/or parts are, in each case, provided with the same reference numerals so that they are not introduced again in each case.

DETAILED DESCRIPTION

Figure 1:
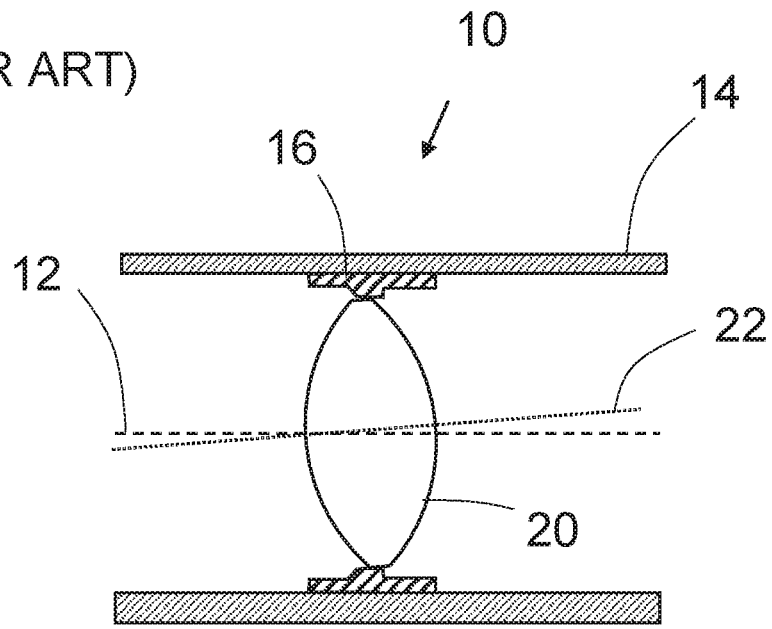
FIG. 1 illustrates a schematic diagram of an optical element in an optical system according to the prior art.
Figure 2:
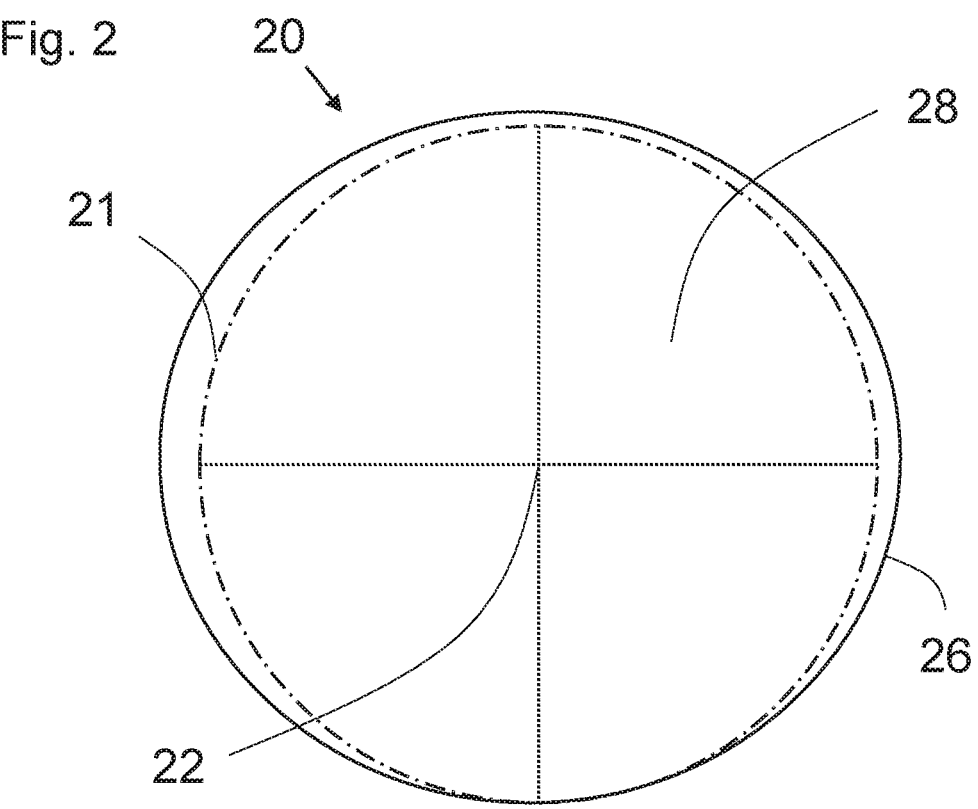
FIG. 2 illustrates a schematic cross-sectional diagram of an optical element before the method is performed.

FIG. 2 schematically shows an optical element 20 in a cross-sectional diagram. The optical element 20 is made of an optically permeable material 28, for example optical glass. The shape of the optical element 20 deviates from the shape of a circle 21. The circle 21 in FIG. 2 is the largest circle with the center point formed by the optical axis 22 and which is still encompassed by the optical element 20.

According to a method for preparing an optical element for insertion into an optical system of an endoscope, the peripheral surface 26 of the optical element is removed such that the peripheral surface 26 follows the circle 21.

Figure 3:
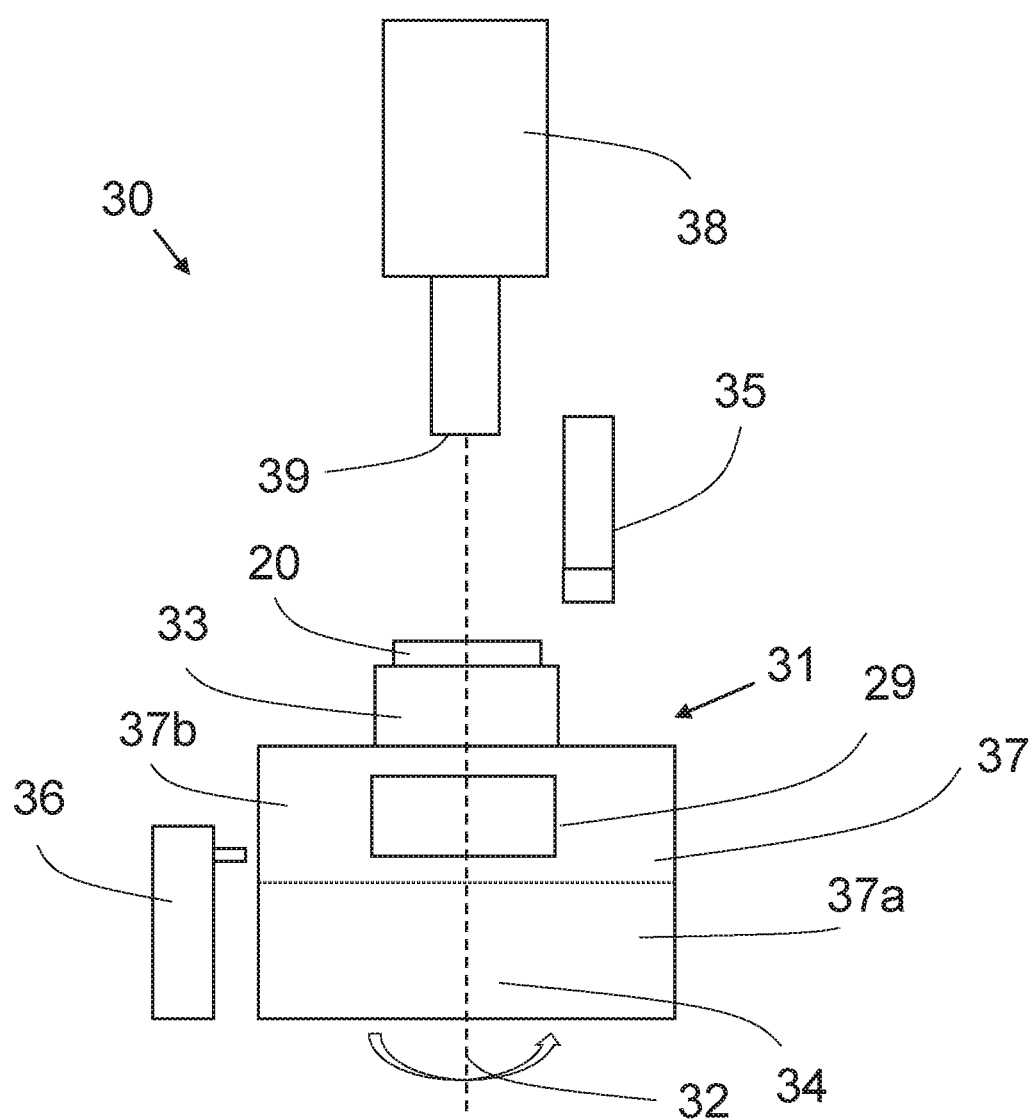
FIG. 3 illustrates a schematic diagram of a centering and rotating device.

FIG. 3 schematically shows a centering and rotating device 30 with which this method can be carried out. The centering and rotating device 30 comprises a spindle 31 which can be rotated about the axis of rotation 32. This is indicated by the arrow arranged about the axis of rotation 32. To ensure that the rotation takes place as evenly as possible, the spindle 31 comprises a hydrostatic bearing 34 that is not shown in more detail in FIG. 3. The spindle 31 also comprises a mounting 33 which holds the optical element 20 to be processed.

The spindle 31 also comprises an alignment unit 37 which has a first part 37a and a second part 37b which are separated in FIG. 3 by the horizontal dotted line. The first part 37a is arranged here such that its alignment to the axis of rotation 32 remains constant. The second part 37b is connected to the mounting 33 and mounted on the first part 37a such that the second part 37b can be tilted in relation to the axis of rotation 32. By means of an impact device 36, impact processes or impacts can be carried out against the second part 37b of the alignment unit 37 such that the alignment of the second part 37b, and thus of the optical element 20, can be changed in relation to the axis of rotation 32. The impact device can be of any type known in the art, such as a piezoelectric actuator or a linear microelectromechanical actuator, such as a comb drive or a solenoid transducer.

Above the optical element 20, a signal detection device 38 is provided which has a photosensitive element 39. By means of the signal detection device 38, the alignment of the optical axis 22 of the optical element 20 in relation to the axis of rotation 32 can be checked in that a light beam is conducted along the axis of rotation 32 from light source 29 through the optical element 20 in the direction of the photosensitive element 39. The photosensitive element can be any type known in the art, such as a CCD or CMOS.

Finally, the centering and rotating device 30 comprises a removal device 35. This uses an ultra-short pulse laser with a wavelength in the femtosecond range as the removal element in the embodiment shown.

FIG. 4a to FIG. 6 describe by way of example a method for preparing an optical element 20 for insertion into an optical system 10 of an endoscope.

Figure 4A:
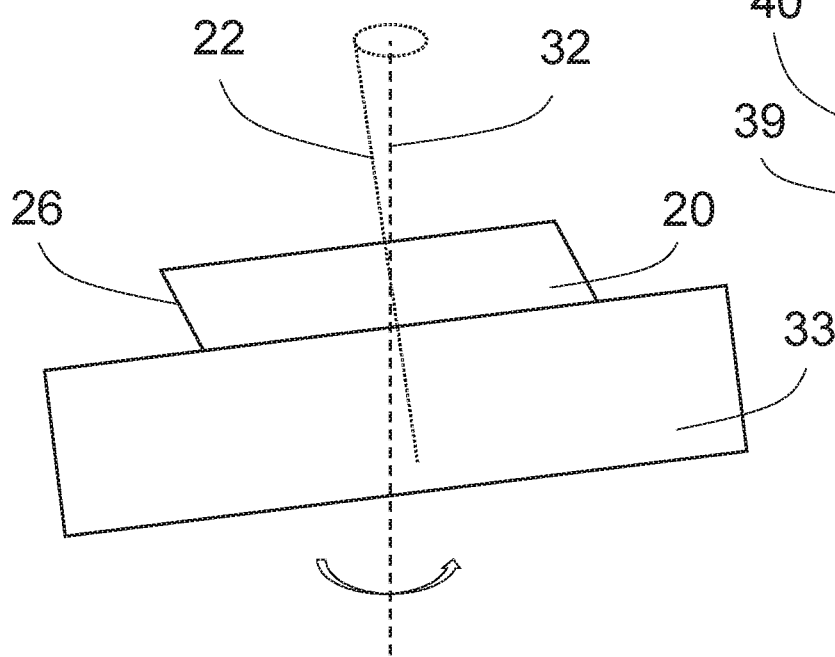
FIG. 4a illustrates a schematic diagram of an optical element on a mounting of a spindle.

FIG. 4a schematically shows an optical element 20 which is held by the mounting 33. The optical axis 22 of the optical element 20 here does not coincide with the axis of rotation 32 of the spindle 31. When the spindle 31 rotates, the optical axis 22 therefore describes a rotating movement about the axis of rotation 32.

Figure 4B:
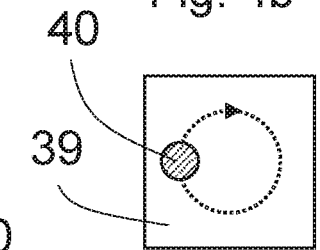
FIG. 4b illustrates a schematic diagram of a photosensitive element with a light signal.

A light beam which is conducted from below along the axis of rotation 32 through the optical element 20 in the diagram in FIG. 4a describes a circular movement on the photosensitive element 40 arranged above the optical element 20, as shown in FIG. 4b.

Figure 5A:
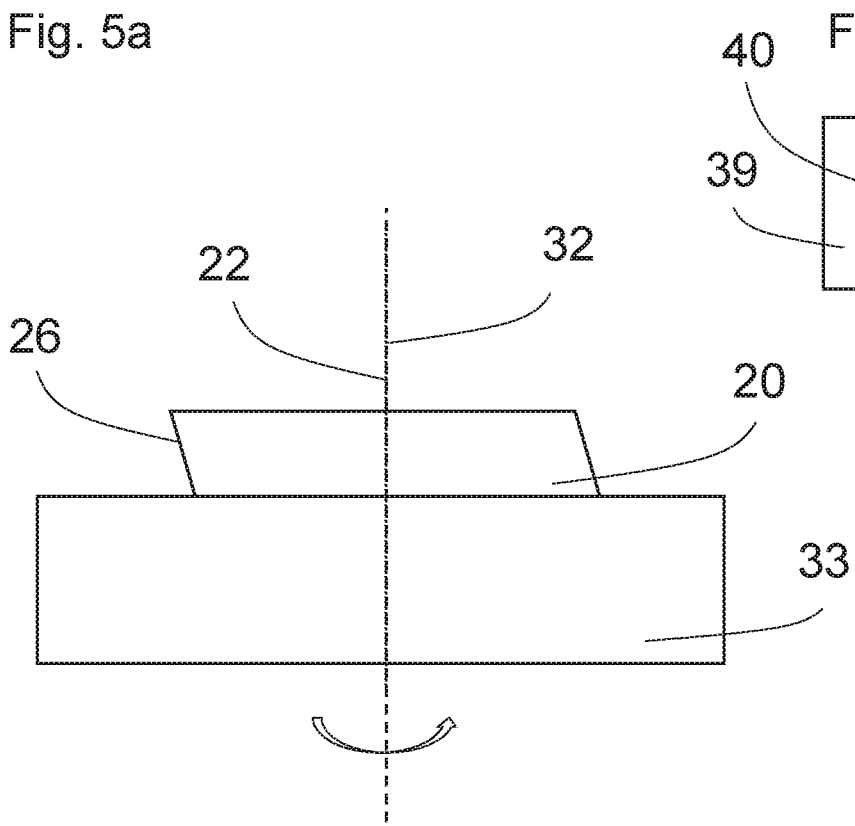
FIG. 5a illustrates a schematic diagram of the optical element on the mounting from FIG. 4a, with coinciding alignment of the optical axis of the optical element and the axis of rotation of the spindle.
Figure 5B:
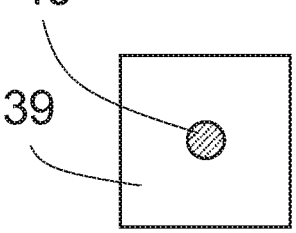
FIG. 5b illustrates a schematic diagram of a photosensitive element with a light signal.

By means of the impact device 36 and the alignment unit 37, the alignment of the optical axis 22 of the optical element 20 on the spindle 31 is changed before the removal of the peripheral surface 26 such that the optical axis 22 of the optical element 20 coincides with the axis of rotation 32 of the spindle 31, as shown in FIG. 5a. FIG. 5b shows how the alignment of the optical axis 22 along the axis of rotation 22 can be checked with the signal detection device 38, since in this case the light signal 40 no longer describes a rotation on the photosensitive element 39.

Figure 6:
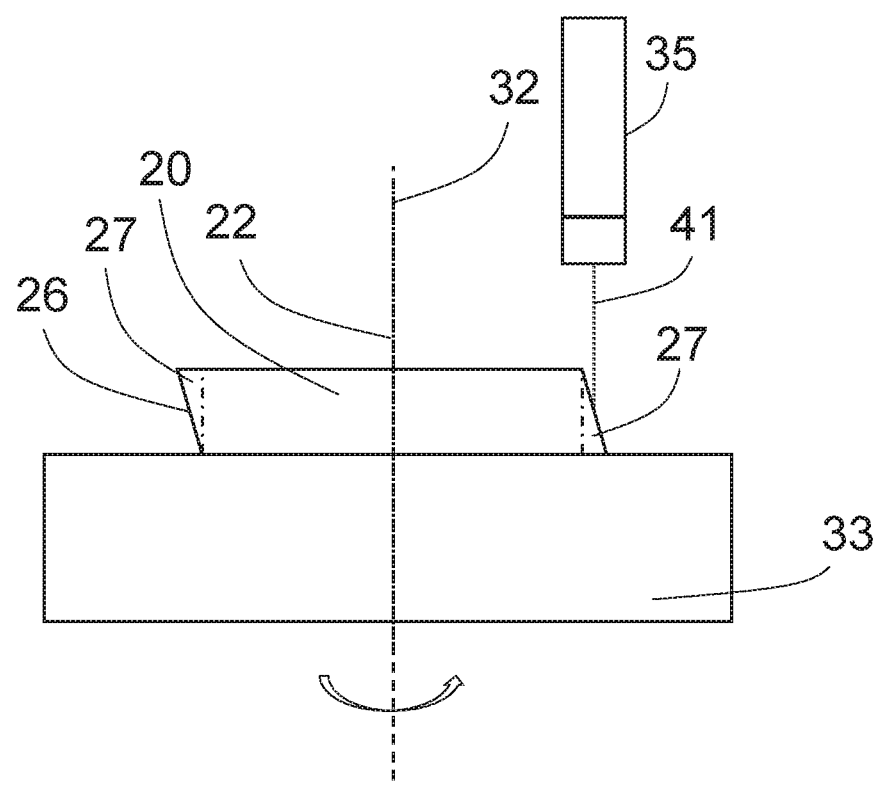
FIG. 6 illustrates a schematic diagram of the optical element on the mounting according to FIG. 5a during a laser ablation.

In FIG. 6, the following removal process is shown schematically. For this, the removal device 35 is arranged such that the outer peripheral surface region 27 of the optical element 20 is removed by means of the ultra-short pulse laser 41.

With the ultra-short pulse laser 41, the optically permeable material 28 of the optical element 20 can be directly removed such that embedding the optical element 20 in a brass sleeve can be omitted.

The deviation of the shape of the optical element 20 and of the alignment of the axis 22 of the optical element 20 shown in FIG. 2 and FIGS. 4a to 6 is shown highly exaggerated for better illustration.

Figure 7:
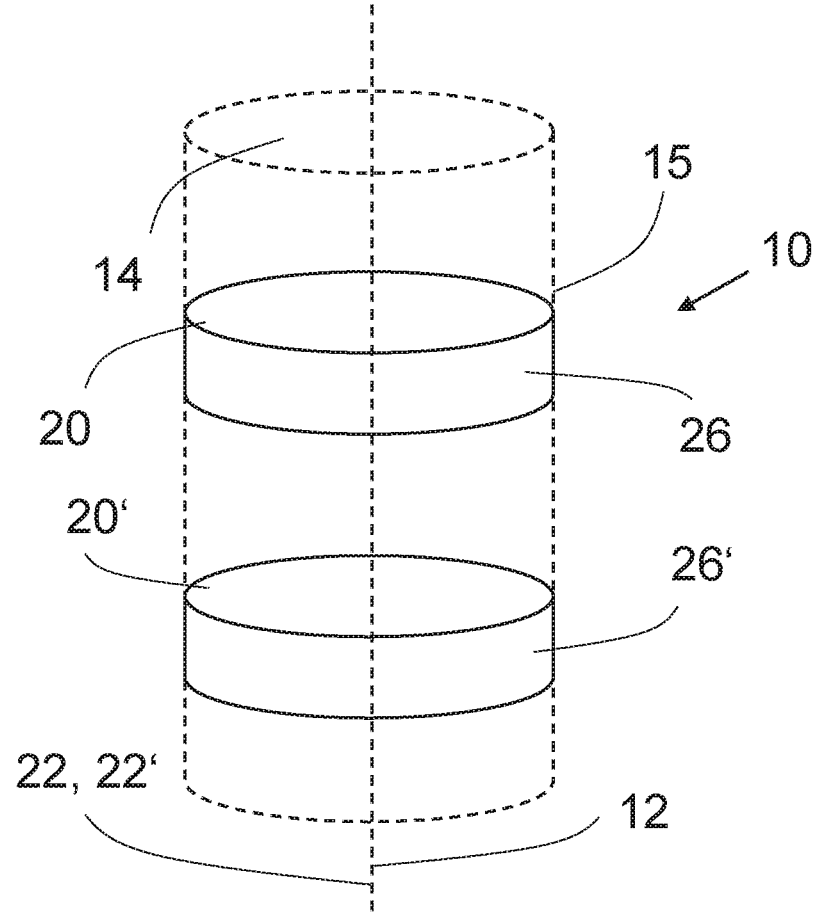
FIG. 7 illustrates two optical elements that have been inserted into an optical frame of an optical system.

In FIG. 7, it is schematically shown how two optical elements 20, 20' are inserted into an optical frame 14 of the optical system 10. The optical frame 14 of the optical system 10 has for this purpose an extremely precisely made inner surface 15, the diameter of which basically corresponds with the diameter of the optical elements 20, 20'. The optical elements 20, 20' are placed into the optical frame 14 such that the peripheral surfaces 26, 26' of the optical elements 20, 20' abut the inner surface 15. In this manner, the optical elements 20, 20' are aligned in the optical system 10 such that the optical axes 22, 22' of the optical elements 20, 20' coincide exactly with the optical axis 12 of the optical system 10.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Optical system
12 Optical axis
14 Optical frame
15 Inner surface
16 Sleeve
20, 20' Optical element
21 Circle
22, 22' Optical axis
26, 26' Peripheral surface
27 Outer peripheral surface region
28 Material
29 Light Source
30 Centering and rotating device
31 Spindle
32 Axis of rotation
33 Mounting
34 Hydrostatic bearing
35 Removal device
36 Impact device
37 Alignment unit
37a First part
37b Second part
38 Signal detection device
39 Photosensitive element
40 Light signal
41 Ultra-short pulse laser

What is claimed is:

1. A method for preparing an optical element for insertion into an optical system of an endoscope, wherein the optical element has an optical axis and a peripheral surface that is basically parallel to the optical axis, the method comprising:
arranging the optical element in a mounting of a spindle which rotates the optical element about an axis of rotation of the spindle,
aligning the optical element on the spindle such that the optical axis of the optical element coincides with the axis of rotation of the spindle, and
subsequent to the aligning, removing an outer peripheral surface region of the optical element until the peripheral surface has a constant spacing from the optical axis of the optical element,
wherein the removing of the outer peripheral surface region takes place by laser ablation.

2. The method according to claim 1, wherein the laser ablation is by an ultra-short pulse laser.

3. The method according to claim 1, wherein the optical element is made of an optically permeable material, and the optically permeable material is removed directly during the removing of the outer peripheral surface region.

4. The method according to claim 1, wherein the aligning of the optical element on the spindle comprises impacting an alignment unit connected to the mounting to change an alignment of the optical axis of the optical element with respect to the axis of rotation of the spindle.

5. The method according to claim 1, further comprising:
checking an alignment of the of the optical element on the spindle by detecting a light signal on a photosensitive element of a signal detection device, wherein the light signal is generated in that a light beam is conducted through the optical element along the axis of rotation of the spindle in a direction of the photosensitive element, and
changing the alignment of the optical element until a position of the light signal on the photosensitive element remains constant when the spindle is rotated.

6. A method for centering an optical element in an optical system of an endoscope, wherein the optical system has an optical axis and the optical element has an optical axis and a peripheral surface that is basically parallel to the optical axis, the method comprising:
removing an outer peripheral surface region of the optical element until the peripheral surface has a constant spacing from the optical axis of the optical element according to the method of claim 1, and
inserting the optical element into the optical system, wherein the peripheral surface of the optical element abuts an inner surface of an optical frame of the optical system and the optical axis of the optical element coincides with the optical axis of the optical system.

7. The method according to claim 6, wherein the optical element comprises multiple optical elements inserted into the optical system, wherein optical axes of each of the multiple optical elements are brought to coincide with the optical axis of the optical system and wherein the peripheral surfaces of each of the optical elements abut the inner surface of the optical frame of the optical system.

8. A centering and rotating device comprising:
a spindle rotatable about an axis of rotation;
a mounting for an optical element for an endoscope disposed on the spindle; and
a removal device with a removal element configured to remove a peripheral surface of the optical element in the mounting, wherein the removal element is an ultra-short pulse laser.

9. The centering and rotating device according to claim 8, further comprising at least one impact device configured to change an alignment of the mounting with respect to the axis of rotation through impacts with an alignment unit connected to the mounting.

10. The centering and rotating device according to claim 8, further comprising at least one signal detection device with a photosensitive element, wherein the photosensitive element is arranged such that a light signal of a light beam conducted along the axis of rotation of the spindle is detected by the signal detection device.

11. The centering and rotating device according to claim 8, wherein the spindle has a hydrostatic bearing.

12. An endoscope comprising:
an optical system having at least one optical element prepared with the method according to claim 1.

13. An endoscope comprising:
an optical system having an optical element centered with the method according to claim 6.

* * * * *